US007785893B2

(12) United States Patent
McEwan et al.

(10) Patent No.: US 7,785,893 B2
(45) Date of Patent: Aug. 31, 2010

(54) METHOD OF CHEMICAL IONIZATION MASS SPECTROMETRY

(75) Inventors: Murray James McEwan, Christchurch (NZ); Paul Francis Wilson, Christchurch (NZ)

(73) Assignee: SYFT Technologies Limited, Christchurch (NZ)

( * ) Notice: Subject to any disclaimer, the term of this patent is extended or adjusted under 35 U.S.C. 154(b) by 916 days.

(21) Appl. No.: 10/520,369

(22) PCT Filed: Jul. 8, 2003

(86) PCT No.: PCT/NZ03/00145

§ 371 (c)(1),
(2), (4) Date: Jun. 15, 2005

(87) PCT Pub. No.: WO2004/006286

PCT Pub. Date: Jan. 15, 2004

(65) Prior Publication Data

US 2005/0255603 A1 Nov. 17, 2005

(30) Foreign Application Priority Data

Jul. 9, 2002 (NZ) ..................................... 520070

(51) Int. Cl.
*G01N 33/00* (2006.01)

(52) U.S. Cl. ....................... 436/139; 436/100; 436/102; 436/106

(58) Field of Classification Search ................... 436/90; 435/135
See application file for complete search history.

(56) References Cited

OTHER PUBLICATIONS

Keough, T. Dimethyl Ether as a Reagent Gas for Organic Functional Group Determination by Chemical Ionization Mass Spectroscopy, 1982, Anal. Chem. vol. 54, pp. 2540-2547.*

Zhu et al. Multiply hydrogen bonded complexes in ether systems: combining experiments with density functional theory calculations, 2000, Int J Mass Spectrom, vol. 194, pp. 93-101.*

Freitas et al. Characterization of ambident electrophile: the gas phase reactivity of the methoxymethyl cation. Int J Mass Spectrom, 1998, vol. 175, pp. 107-122.*

Wilson, P.F. et al, "Reactions of $CH_3OCH_2^+$ with Hydrocarbons and O, N, and S Compounds: Applications for Chemical Ionization in Selected Ion Flow Tube Studies," J. Am. Soc. Mass Spectrom. (2002), 13, pp. 1028-1033.

Da Silva, M.V. et al, "*Like* double resonance experiments for studying precursor and intermediate ions involved in ion-molecule reactions produced under self-ionization conditions," Proceedings of the 49$^{th}$ ASMS Conference on Mass Spectrometry and Allied Topics, Chicago, Illinois, May 27-31, 2001.

Tu, Ya-Ping et al, "Stereochemical Effects in Mass Spectrometry: Part 8—Chemical Ionization Mass Spectra of Cyclic Glycols and Monosaccharides Using Formaldehyde Dimethyl Acetal as Reagent Gas," Organic Mass Spectrometry (1990), 25, pp. 9-13.

* cited by examiner

*Primary Examiner*—Yelena G Gakh
*Assistant Examiner*—David Weisz
(74) *Attorney, Agent, or Firm*—Steptoe & Johnson LLP

(57) ABSTRACT

A method of detecting a substance present in a gas or a gas mixture using SIFT-MS technology comprising the steps of inducing a supply of alkoxymethyl cations into the inlet of the flow tube, reacting a sample of the as with the alkoxymethyl cations, analysing the reacted gas sample, and calculating the concentration of trace levels of molecules containing heteroatoms in the reacted gas sample.

4 Claims, 1 Drawing Sheet

METHOD OF CHEMICAL IONIZATION MASS SPECTROMETRY

TECHNICAL FIELD

The present invention relates to a method for detecting any of a number of substances present in gases or gas mixtures containing alkanes, ethane or ethyne, using chemical ionization mass spectrometry.

BACKGROUND ART

Chemical ionization mass spectrometry has been used for analyte identification since the development of mass spectrometry [Munson, M. S. B.; Fjeld, F. H. *J. Amer. Chem. Soc.,* 88, 2621-2630 (1966); Munson, M. S. B.; Field, F. H. *J. Amer. Chem. Soc.,* 88, 337-4345, (1966); Munson, M. S. B.; Field, F. H. *J. Amer. Chem. Soc.,* 89, 1047-1052, (1967)]. In recent years instruments utilizing chemical ionization sources have been marketed for analysis of gas mixtures [Linforth, R.; Preece, S. *Technical Note* 236, Micromass Ltd, (1998); Adechy, M.; Shress, V.; Squibb, A. Peak, 1, 2-4, (2000)]. The combination of a chemical ionization source with flow tube reactor techniques allows both identification and quantification of trace species without internal calibration. Two closely related systems have been developed using this combination of techniques; *Proton Transfer Mass Spectrometry* [Lindinger, W.; Hansel, A.; Jordan, A. Int. J. Mass Spectrom; Jon Proc., 173, 191-241, {1998)] and *Selected Ion Flow Tube Mass Spectrometry* [Spanel, P.; Smith, D. Mea Bioi. Eng. Comput., 34, 409-419, (1996)].

The selection of the chemical ionizing agent or precursor ion is critical to the application of the technique. The precursor ion must be reactive with the analyte molecule(s) but unreactive with the bulk gas within which the analyte is present as a trace component. In most applications to date the bulk gas is ambient air or exhaled breath and the analyte species are various Volatile Organic Compounds (VOCs).

Precursor ions which have been in common use include $NO^+$, $O_2^+$, $NH4^+$ and $OH^-$ A further important criterion for selection of a chemical ionization precursor is the facility with which it can be generated in large amounts using typical instrumentation such as an electron impact or microwave discharge source.

It is known from previous experimental work (Freitas, M. A. O'Hair, R. A. J. Int. J. Mass Spectrom; Ion Proc 1998, 175, 102-122) that the methoxymethyl cation is not reactive with alkanes but will react with molecules containing heteroatoms. However, the use of $CH_3OCH_2^+$ as a chemical ionization reagent for quantification and identification of analytes has not been tried previously.

DISCLOSURE OF INVENTION

In one form the invention is a method of detecting and quantifying trace levels of molecules containing one or more of a range of reactive species, in gases or gas mixtures consisting of alkanes, ethene, or ethyne, said method including using an alkoxyalkyl cation as the chemical ionisation precursor in a selected ion flow tube mass spectrometer.

Preferably the method further includes reacting the sample gas to be analysed with the alkoxyalkyl cation in a stream of helium in the flow tube.

Preferably the alkoxyalkyl cation is a methoxymethyl cation.

The invention in another aspect comprises a method of detecting and quantifying a gas sample containing trace levels of molecules containing one or more of a range of reactive species, in gases or gas mixtures consisting of alkanes, ethene, or ethyne in a selected ion flow tube mass spectrometer comprising the steps of:

producing a supply of alkyoxymethyl cations, mass electing the alkyoxymethyl cations, inducing a flow of the alkyoxymethyl cations into the inlet of a flow tube of the spectrometer in a carrier flow of helium reacting the gas sample with the alkyoxymethyl cations, analysing the reacted gas sample in the mass spectrometer, and calculating the concentration of the trace levels of molecules containing heteroatoms present in the reacted gas sample.

Preferably the alkyoxymethyl cation is a methoxymethyl cation.

Preferably the range of reactive species includes molecules that contain sulphur, nitrogen, oxygen, phosphorus or silicon heteroatoms,

BRIEF DESCRIPTION OF DRAWINGS

By way of example only, a preferred embodiment of the present invention is described in detail with reference to the accompanying flow chart.

BEST MODE OF CARRYING OUT THE INVENTION

Figure 1:
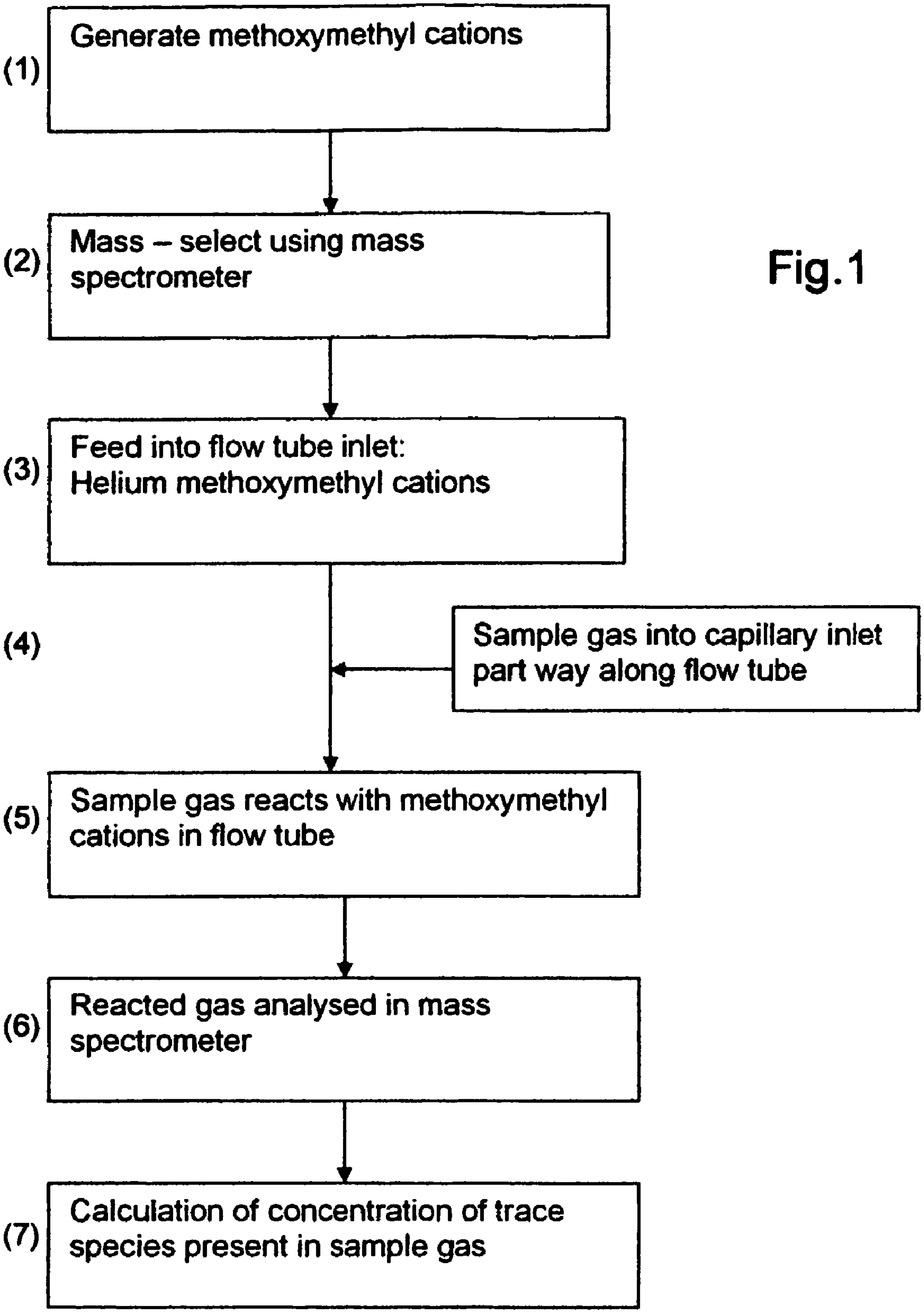

Referring to the flow chart, in step 1, a supply of methoxymethyl cations is produced. This may be done by any of a number of known methods, for example, using the helium flowing afterglow method in which a stream of helium gas is passed in a pyrex or quartz tube through a microwave discharge and a small amount of dimethoxymethane is added to the gas stream emerging from the tube. Methoxymethyl cations are produced by a reaction between the helium metastable species and the dimethoxymethane.

Another process which may be used to produce the methoxymethyl cations is electron impact using an incandescent rhenium filament within a vacuum chamber filled with a low pressure dimethoxymethane.

In step 2, the methoxymethyl cations are mass selected, using a mass spectrometer.

In step 3, the methoxymethyl cations are introduced into the inlet of a flow tube in a carrier flow of helium, at ambient temperature and at a pressure of about 0.5 Torr.

As the mixture of helium and methoxymethyl cations flow along the flow tube, the sample gas to be analysed is introduced into the flow tube via a capillary inlet (step 4).

In step 5, the methoxymethyl cations react with the gas sample, which is primarily one or more alkane gases, but which also contains traces of molecules containing heteroatoms, (e.g. sulphur, nitrogen). This type of gas sample is typical of the type of sample from a leaking gas pipe.

The methoxymethyl [$CH_3OCH_2^{+]}$ ion is unreactive with alkanes, ethene and ethyne, i.e. the hydrocarbons that are present as bulk constituents of natural gas and other hydrocarbon fuel mixtures viz methane, $CH_4$; ethane, $C_2H_6$; propane, $C_3H_8$; butane, $C_4H_{10}$; ethylene, $C_2H_4$ and acetylene, $C_2H_2$. The $CH_3OCH_2$ ion is, however, reactive with many sulfur-containing and nitrogen-containing species, including methanethiol, $CH_3SH$; ethanethiol, $C_2H_5SH$; dimethylsulfide, $(CH_3)_2S$ and diethylsulfide, $(C_2H_5)_2S$.

The reactivity of $CH_3OCH_2^+$ with selected neutral species in a pressure of 0.5 Torr of helium at room temperature is shown in Table 1.

TABLE 1

| Neutral | Products | Branching Ratio | Reaction Rate $10^{-9}$ $cm^3$ $s^1$ |
|---|---|---|---|
| $O_2$ | No reaction | | <0.0005 |
| $N_2$ | No reaction | | <0.0005 |
| $H_2O$ | No reaction | | <0.0005 |
| CO | No reaction | | <0.0005 |
| $CO_2$ | No reaction | | <0.0005 |
| Ar | No reaction | | <0.0005 |
| $CH_4$ | No reaction | | <0.0005 |
| $C_2H_6$ | No reaction | | <0.0005 |
| $C_3H_6$ | No reaction | | <0.0005 |
| $C_3H_8$ | No reaction | | <0.0005 |
| $C_4H_{10}$ | No reaction | | <0.0005 |
| $C_2H_2$ | No reaction | | <0.0005 |
| $C_2H_4$ | No reaction | | <0.0005 |
| $CH_3SH$ | $CH_3OCH_2{\bullet}CH_3SH^+$ | (0.95) | 0.31 |
| | $CH_3SHCH^+ + CH_3OH$ | | |
| $C_2$H5SH | $CH_3OCH_2{\bullet}C_2H_5SH$ | (0.15) | 0.90 |
| | $C_2H_5SHCH^+ + HCHO$ | (0.85) | |
| $(CH_2)_2S$ | $CH_3OCH_2{\bullet}(CH_3)_2S^+$ | (0.95) | 1.4 |
| | $(CH_3)_2{\bullet}SCH_3{}^+ +$ HCHO | (0.05) | |
| (C2H5)2s | $CH_3OCH_2{\bullet}(C_2H_5)_2$s+ | (1.0) | 1.9 |

The reacted gas sample produced in step 5 is then analysed in known manner in a mass spectrometer (step 6). Since the methoxymethyl cations react only with the molecules containing the heteroatoms, analysis of the mass spectrometry results can be used to calculate the concentration of the trace species containing heteroatoms present in the alkane gases.

Although the preferred alkoxyalkyl cation is highly preferred, other oxy-radicals can also be employed. For example, but without limiting suitable oxy-radicals are peroxynitrite, alkoxy cations and reactive oxygen species such as HOCl can be employed with appropriate substrates.

One application of the method herein described is to enable leaks of gas from gas lines or gas containers to be easily and simply detected. Producers of gas often add substances containing sulphur or other odiferous material to gas to aid the detection of leaks, and it is very useful to be able to detect small leaks by detecting the very small quantities of the sulphur-containing or other added material. For this, it is necessary to have a detection method which reacts with the sulphur-containing or other added material but does not react with the bulk gas or with the major constituents of air, It will be appreciated that the detection of leaks from has lines is only one of many applications resulting from the present invention and the method of the present invention has an application in many other fields.

Because the method as herein described uses SIFT-MS technology, it is possible to identify and quantify the reaction product, ethylene, of the methoxymethyl radical reaction with the substrate. In addition it is possible to carry out the identification and quantification in 'real time' and so can be used to characterise the kinetics of the oxyradical-substrate interaction. Consequently it is possible to make quantitative and kinetic comparisons between different reaction mixtures.

Having disclosed preferred forms of the invention, it will be apparent to those skilled in this particular art that modifications and changes can be made to various parameters and yet still come within the general concept of the invention. All such modifications and changes are intended to be included in the scope of the invention.

The invention claimed is:

1. A method of detecting and quantifying trace levels of molecules containing one or more of a range of reactive species in gases or gas mixtures containing alkanes, ethene, or ethyne, said method including using a short chain alkoxymethyl cation as the chemical ionization precursor in a selected ion flow tube mass spectrometer wherein the chemical ionization precursor does not react with the major components of air, nor with the gas or the gas mixtures containing alkanes, ethene or ethyne but reacts with the trace levels of molecules to be detected, wherein the trace levels of molecules to be detected comprises molecules containing sulfur or nitrogen heteroatoms.

2. The method as claimed in claim 1, further including reacting the sample gas to be analysed with the alkoxymethyl cation in a stream of helium in the flow tube.

3. The method as claimed in claim 1, wherein the alkoxymethyl cation is a methoxymethyl cation.

4. A method of detecting and quantifying a gas sample containing trace levels of molecules containing one or more of a range of reactive species in gases or gas mixtures containing alkanes, ethene, or ethyne in a selected ion flow tube mass spectrometer comprising the steps of: producing a supply of methoxymethyl cations, mass selecting the methoxymethyl cations, inducing a flow of the methoxymethyl cations into the inlet of a flow tube of the spectrometer in a carrier flow of helium reacting the gas sample with the methoxymethyl cations, analysing the reacted gas sample in the mass spectrometer, and calculating the concentration of the trace levels of molecules containing heteroatoms present in the reacted gas sample wherein the methoxymethyl cations do not react with the major components of air, nor with the gas or the gas mixtures containing alkanes, ethene or ethyne but reacts with the trace levels of molecules to be detected, wherein the trace levels of molecules to be detected comprises molecules containing sulfur or nitrogen heteroatoms.

* * * * *